(12) United States Patent
Decoodt et al.

(10) Patent No.: US 8,049,055 B2
(45) Date of Patent: Nov. 1, 2011

(54) PROCESS AND DEVICE FOR SEPARATION IN A SIMULATED MOVING BED WITH A BYPASS FLUID FLOW RATE THAT IS NOT REGULATED AUTOMATICALLY

(75) Inventors: Xavier Decoodt, Carrieres S/Seine (FR); Gerard Hotier, Rueil Malmaison (FR); Philibert Leflaive, Mions (FR); Damien Leinekugel Le Cocq, Lyons (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 198 days.

(21) Appl. No.: 12/543,091

(22) Filed: Aug. 18, 2009

(65) Prior Publication Data

US 2010/0048973 A1 Feb. 25, 2010

(30) Foreign Application Priority Data

Aug. 19, 2008 (FR) ...................................... 08 04638

(51) Int. Cl.
*C07C 7/12* (2006.01)
(52) U.S. Cl. .......................... 585/828; 585/820; 585/827
(58) Field of Classification Search .................. None
See application file for complete search history.

(56) References Cited

U.S. PATENT DOCUMENTS

| | | | |
|---|---|---|---|
| 5,882,523 A | 3/1999 | Hotier et al. | |
| 5,972,224 A | 10/1999 | Hotier et al. | |
| 6,110,364 A | 8/2000 | Hotier et al. | |
| 6,537,451 B1 | 3/2003 | Hotier | |
| 2003/0127394 A1* | 7/2003 | Hotier | 210/661 |
| 2008/0041788 A1* | 2/2008 | Hotier et al. | 210/659 |
| 2010/0258505 A1* | 10/2010 | Decoodt et al. | 210/661 |

FOREIGN PATENT DOCUMENTS

| | | |
|---|---|---|
| EP | 0 821 988 A1 | 2/1998 |
| FR | 2 794 836 A1 | 12/2000 |

OTHER PUBLICATIONS

Search Report of FR 08/04638 (Mar. 9, 2009).

* cited by examiner

*Primary Examiner* — Tam M Nguyen
(74) *Attorney, Agent, or Firm* — Millen, White, Zelano & Branigan, P.C.

(57) ABSTRACT

Process for separation of a feedstock F by adsorption in a simulated moving bed in an SMB device that comprises a zone 1 for desorption of compounds produced by extraction, a zone 2 for desorption of compounds produced with a raffinate, a zone 3 for adsorption of compounds produced by extraction, and a zone 4 that is located between the draw-off of the raffinate and the supply of the desorbent, whereby the device comprises external bypass lines $L_{i/i+1}$ directly joining two successive plates $P_i$, $P_{i+}$, that are equipped with non-automated means for adjusting flow rate and closing means, in which the degree of opening of the restriction means of the scavenging flow rate of the bypass lines $L_{i/i+1}$ is adjusted so as to obtain the best performance of the SMB.

3 Claims, 4 Drawing Sheets

PROCESS AND DEVICE FOR SEPARATION IN A SIMULATED MOVING BED WITH A BYPASS FLUID FLOW RATE THAT IS NOT REGULATED AUTOMATICALLY

FIELD OF THE INVENTION

The invention relates to the field of the separations of natural or chemical products that cannot easily be separated by distillation. A family of processes, and associated devices, known under the name of processes or devices for separation in a simulated moving bed or in simulated countercurrent or in simulated co-current, to which we will refer below by the name "SMB," are then used.

The fields in question are in particular, and non-exclusively:

The separation between, on the one hand, normal paraffins, and, on the other hand, branched paraffins, naphthenes, and aromatic compounds, The olefins/paraffins separation, The separation of paraxylene from other isomers into C8 aromatic compounds, The separation of metaxylene from other isomers into C8 aromatic compounds, The separation of ethylbenzene from other isomers into C8 aromatic compounds.

Away from the refinery and petrochemical complex, there are numerous other applications among which it is possible to cite the glucose/fructose separation, the separation of the positional isomers of cresol, optical isomers, etc.

PRIOR ART

The SMB separation is well known in the prior art. As a general rule, a column that operates in a simulated moving bed comprises at least three zones and optionally four or five, whereby each of these zones consists of a certain number of successive beds, and each zone is defined by its position between one supply point and one draw-off point. Typically, an SMB column is supplied by at least one feedstock F that is to be fractionated and a desorbent D (sometimes called an eluant), and at least one raffinate R and one extract E are drawn off from said column.

The supply points and draw-off points are modified over time, typically offset in the same direction by a value corresponding to a bed.

By definition, each of the operational zones is designated by a number:

Zone 1=zone for desorption of the compounds of the extract, between the injection of the desorbent D and the draw-off of the extract E;

Zone 2=zone for desorption of the compounds of the raffinate, between the draw-off of the extract E and the injection of the feedstock to be fractionated F;

Zone 3=adsorption zone of the compounds of the extract, between the injection of the feedstock and the draw-off of the raffinate R;

And preferably a zone 4 that is located between the draw-off of the raffinate and the injection of the desorbent.

In an in-depth manner, the prior art describes different devices and processes that make it possible to carry out the separation of feedstocks in a simulated moving bed.

It is possible to cite in particular the U.S. Pat. Nos. 2,985,589, 3,214,247, 3,268,605, 3,592,612, 4,614,204, 4,378,292, 5,200,075, and 5,316,821. These patents also describe in detail the operation of an SMB.

The SMB devices typically comprise at least one column (and often two), divided into several successive adsorbent beds $A_i$, whereby said beds are separated by plates $P_i$, each plate $P_i$ comprising one, two or four chambers making it possible to carry out sequential operations for supplying the feedstock or for injection of the desorbent and extraction of the raffinate or the extract.

A single chamber can carry out the four operations, but this invention relates to the columns with two chambers per plate. Several solutions are possible for the use of two chambers, each able to be used for the injection or the draw-off of one or more flows. For example, a first chamber can carry out operations for injection of feedstock or desorbent, and the other chamber carries out operations for drawing-off raffinate or extract. Another possible illustrative case consists in using a chamber for the injection of the feedstock and the draw-off of the raffinate, the other managing the injection of desorbent and the draw-off of the extract. These two examples are not limiting, whereby other uses of the two chambers are possible.

The controlled means for distribution and extraction of fluids of an SMB are typically one of the following two major types of technology:

Either, for each plate, a number of all-or-nothing controlled valves for the supply or the draw-off of fluids, whereby these valves are typically located in the immediate vicinity of the corresponding plate. Each plate $P_i$ typically comprises at least four all-or-nothing controlled two-way valves to carry out respectively the supply of fluids F and D and the draw-off of fluids E and R, Or a multi-path rotary valve for the supply or the draw-off of fluids on the set of plates.

This invention relates to the framework of the SMB units that use a number of valves to ensure the supply and the draw-off of the different fluids.

Each of the plates $P_i$ typically comprises a number of distributor-mixer-extractor panels, called "DME plates," which are supplied by distribution/extraction lines or systems. The plates can be of any type and of any geometry. They are generally divided into panels, corresponding to adjacent sectors of the section of the column, for example panels with angular sectors as presented in the U.S. Pat. No. 6,537,451, FIG. 8, or panels with parallel sectors such as cut out in a circumference as the U.S. Pat. No. 6,797,175 describes.

Preferably, the separation column according to the invention comprises DME plates of the type with parallel sectors and asymmetrical feeds.

The distribution on each of the beds requires a collection of the primary flow that is obtained from the preceding bed, the possibility of injecting there an accompanying fluid or a secondary fluid while mixing these two fluids as well as possible, or else the possibility of sampling a portion of the collected fluid, of extracting it to send it to the outside of the device and also to redistribute a fluid to the next bed.

A generic problem of all of the SMB devices is to minimize the pollution that is generated by the liquid that is found in the different zones of the circuit(s) for supply and draw-off of fluids of the plates, during modifications of the supply and draw-off points during the operation of the SMB.

Actually, when, during the operating sequence, a line, chamber or supply zone of a plate $P_i$ is no longer flushed by a fluid of the process, it becomes a dead zone in which the liquid stagnates, and it is only put back into motion when another fluid of the process circulates there again. Owing to the operation of the SMB, it then involves a fluid of the process that is generally different from the fluid that is stagnating in the line under consideration.

The mixing, or the circulation of fluids of significantly different compositions for a short time, introduces disruptions in the profiles of concentration of the zone considered relative to the ideal operation, for which the discontinuities of composition are to be proscribed.

Another problem resides in the possible recirculation between different zones of the same plate, and more generally of the entire distribution/extraction system of the same plate, because of very small pressure differences between the different zones of the plate, which also induces a disturbance relative to the ideal operation.

To solve these problems that are linked to recirculation and to dead zones, different techniques are known from the prior art:

a) It is proposed to carry out a flushing of the distribution/extraction system of a plate that is provided by desorbent or the desired, relatively pure product. This technique actually makes it possible to prevent the pollution from the desired product during its extraction. However, since the flushing liquid has a very different composition from the liquid that it displaces, this introduces composition discontinuities that are detrimental to ideal operation. This first flushing variant typically produces flushing cycles of short duration with a high concentration gradient. These flushing cycles are of short duration specifically to limit the effects of the composition discontinuities.

b) Another solution consists in, as described in the U.S. Pat. Nos. 5,972,224 and 6,110,364, sending a majority of the primary flow toward the inside of the column and a minority of this flow (typically 1% to 20% of the primary flow) toward the outside via external bypass lines between successive plates. This flushing of the distribution/extraction system at a plate by a flow that is obtained from the upper plate is typically carried out continuously, such that the lines and zones of the distribution/extraction system are no longer "dead," but are constantly flushed.

Such a system with continuous flushing via bypass lines is shown in FIG. 2 of the patent FR 2,772,634.

According to the teaching of U.S. Pat. Nos. 5,972,224 and 6,110,364, it is desired to carry out a flushing of the distribution/extraction system of a given plate by liquid that has a composition that is very close to that of the displaced liquid (liquid that is present in this distribution system or that circulates at the plate). Thus, the mixing of fluids of different composition is minimized, and the composition discontinuities are reduced.

For this purpose, the U.S. Pat. Nos. 5,972,224 and 6,110,364 recommend implementing flushing flows in the bypasses so that the transit speed in each bypass is essentially the same as the speed of advance of the concentration gradient in the primary flow of the SMB. The process is then referred to as "synchronous" flushing or a flushing "with synchronous flow rate." Thus, a flushing of different lines and capacities is carried out by a fluid that has a composition that is essentially identical to that of the liquid that is found there, and the liquid that circulates in a bypass is reintroduced at a point where the composition of the primary flow is essentially identical. Synchronous flushing cycles of long duration with a low or zero concentration gradient are therefore carried out.

According to the teaching of this patent, a flushing is referred to as "synchronous" when the flushing flow rate $QS_{i/i+1}$ that is obtained from a plate $P_i$ to the next plate $P_{i+1}$ is equal to V/ST in which V is the cumulative volume of the distribution systems of the plates $P_i$ (or $V_i$) and $P_{i+1}$ (or $V_{i+1}$) and the volume of the bypass line between these two plates (or $VL_{i/i+1}$) and ST is the period of the cycle of the SMB (between two successive switchings of the feed/extraction).

There is therefore:

Synchronous flow rate=$QS_{i/i+1}$=$(V_i+V_{i+1}+VL_{i/i+1})/ST$, with:

$QS_{i/i+1}$=flushing flow rate that is obtained from the plate $P_n$ to the adjacent plate (typically lower) $P_{i+1}$;

$V_i$=Volume of the distribution/extraction system of the starting plate $P_i$;

$V_{i+1}$=Volume of the distribution/extraction system of the intake plate $P_{i+1}$;

$VL_{i/i+1}$=Volume of the bypass line between $P_i$ and $P_{i+1}$;

ST=Switching period.

The implementation of the synchronous flushing is typically carried out using a flushing with a controlled flow rate, ranging from 50% to 150% of the synchronous flow rate in these zones, and ideally 100% of the synchronous flow rate. The flow rates of the bypass lines of these 4 zones are monitored by regulation means in each bypass line.

Regulation means on each bypass line represent a costly unit, however, and this invention proposes defining a process and an associated adjustment method making it possible to obtain very good performances of the unit without an automatic regulation means on the flushing lines.

The applicant showed that the teachings of "synchronous flushing cycles" of the U.S. Pat. Nos. 5,972,224 and 6,110,364 provide an obvious improvement relative to the prior art but require the implementation of regulating means in each bypass line, which generates a significant cost.

One of the objects of this invention is to eliminate this drawback by limiting the number of regulating chains and control valves.

Another object of the invention is to show that it is possible in some cases, surprisingly enough, also to improve the operation and the performances of the process for separation in a simulated moving bed by refining the rules of definition of the different flow rates of the bypass lines relative to the prior art while limiting the number of regulating chains and control valves.

BRIEF DESCRIPTION OF THE INVENTION

The first object of the invention is to limit the number of regulating chains and control valves in the bypass lines relative to the teaching of the U.S. Pat. Nos. 5,972,224 and 6,110, 364 by using non-automated means for adjusting flow on the bypass lines. Another object of the invention is to improve the performances of a process for separation in a simulated bed relative to the teaching of these same patents.

The invention also relates to an improved device for separation in a simulated moving bed that uses a number of all-or-nothing controlled two-way valves for the supply and extraction of process fluids of the SMB and that carry out flushing cycles of long duration with a low or zero concentration gradient.

It has actually been discovered, surprisingly enough, that the use of a flow rate that is not strictly synchronous to all of the operating zones of the SMB but with a flow rate that is differentiated according to the zones of the SMB and that therefore can have, in some cases, an under- or over-synchronicity that is more or less marked, made it possible to obtain a good performance of the SMB.

Even more surprisingly, it was discovered that in some cases, the use of a flow rate that can therefore have an under- or over-synchronicity that is more or less marked made it possible to obtain a performance of the SMB that is greater than the one that is obtained with a flow rate that is strictly synchronous to all of the operating zones of the SMB.

Under-synchronicity is defined as a value that is less than the value that corresponds to the synchronicity of at least 10% (that is expressed as a percentage below said synchronicity), and over-synchronicity is defined as a value that exceeds the value that corresponds to the synchronicity of at least 10% (that is expressed as a percentage above said synchronicity).

More specifically, this invention can be defined as a process for separation in a simulated moving bed (SMB) of a feedstock F in an SMB device that has at least one column, whereby said column consists of a number of adsorbent beds that are separated by plates $P_i$, each comprising a distribution/extraction system, a process in which the feedstock F and a desorbent D are supplied, and at least one extract E and at least one raffinate R are drawn off, whereby the supply and draw-off points are offset over time by a value that corresponds to an adsorbent bed with a switching period ST, and that determines a number of operating zones of the SMB, and in particular the four following primary zones:

A zone 1 for desorption of the compounds that are produced by extraction, between the supply of the desorbent D and the draw-off of the extract E, A zone 2 for desorption of the compounds that are produced with raffinate, between the draw-off of the extract E and the supply of the feedstock F, A zone 3 for the adsorption of the compounds that are produced by extraction, between the supply of the feedstock and the draw-off of the raffinate R, A zone 4, located between the draw-off of the raffinate R and the supply of the desorbent D, whereby the device also comprises external bypass lines $L_{i/i+1}$ directly joining two successive plates $P_i$, $P_{i+1}$ that allow the flushing of said plates, in which each of the bypass lines $L_{i/i+1}$ comprises non-automated means for adjusting the flushing flow rate, whereby the degree of opening of said adjusting means is the same for all of the bypass lines of the SMB device and determined so as to obtain the highest yield of desired product with fixed desorbent flow rate, feedstock flow rate, purity of the desired product and switching period, or the highest purity of the desired product, with fixed desorbent flow rate, feedstock flow rate, yield of desired product and switching period.

In a second variant of the process for separation in a simulated moving bed (SMB) according to the invention, the degree of opening of non-automated means for adjusting the flushing flow rate of the bypass lines is determined so as to obtain the lowest desorbent flow rate with purity and yield of the desired product, with fixed switching time and feedstock flow rate.

In a third variant of the process for separation in a simulated moving bed (SMB) according to the invention, the degree of opening of the non-automated means for adjusting the flushing flow rate of the bypass lines is determined so as to obtain the highest flow rate of feedstock with the purity and yield of the desired product, and with fixed switching time and desorbent flow rate.

The process for separation in a simulated moving bed according to the invention applies in particular to the separation of paraxylene within a mixture of C8 aromatic hydrocarbons or to the separation of metaxylene within a C8 hydrocarbon mixture.

DETAILED DESCRIPTION OF THE INVENTION

So as to limit the number of regulating chains and control valves, in particular on the bypass lines, the invention proposes a process for separation in a simulated moving bed (SMB) of a feedstock F in an SMB device that has at least one column, whereby said column consists of a number of adsorbent beds that are separated by plates $P_i$, each comprising a distribution/extraction system, a process in which the feedstock F and a desorbent D are supplied, and at least one extract E that is rich in a desired product and at least one raffinate R are drawn off, whereby the supply and draw-off points are offset over time by a value that corresponds to an adsorbent bed with a switching period ST and determine a number of operating zones of the SMB, and in particular the following four primary zones:

A zone 1 for desorption of the compounds of the extract, between the supply of the desorbent D and the draw-off of the extract E;

A zone 2 for desorption of the compounds of the raffinate, between the draw-off of the extract E and the supply of the feedstock F;

A zone 3 for the adsorption of the compounds of the extract, between the supply of the feedstock and the draw-off of the raffinate R;

A zone 4 that is located between the draw-off of the raffinate R and the supply of the desorbent D.

The device also comprises external bypass lines $L_{i/i+1}$ directly joining two successive plates $P_i$, $P_{i+1}$ that allow the flushing of said plates.

Each of these bypass lines $L_{i/i+1}$ comprises non-automated means for adjusting the flushing flow rate such as manual control valves, whose degree of opening is predetermined, or calibrated restriction openings.

The external bypass line $L_{i/i+1}$ directly joining two successive plates $P_i$, $P_{i+1}$ is said to belong to a zone when the bed between the plates $P_i$ and $P_{i+1}$ belongs to said zone.

A bypass line is said to be closed when the flow rate in this bypass line is zero. This closing can be carried out using any technical means that makes it possible to cancel the flow rate in the bypass line, such as in particular an all-or-nothing valve.

The degree of opening of said non-automated adjusting means is adjusted so as to obtain the best performance of the SMB. The performance level of the SMB can be measured in different ways.

The performance can be measured in terms of yield of desired product with fixed desorbent flow rate, feedstock flow rate, purity of the desired product and switching period. The higher the yield, the better the performance of the SMB. This method is the one most commonly used.

The performance can also be measured in terms of purity of the desired product with fixed desorbent flow rate, feedstock flow rate, yield of desired product and switching period. The higher the purity, the better the performance of the SMB.

Another way of measuring the performance of the SMB is to measure the flow rate of desorbent with purity and yield of the desired product, with fixed switching time and feedstock flow rate. The lower this desorbent flow rate, the better the performance of the SMB.

Another way of measuring the performance of the SMB is to measure the flow rate of the feedstock with purity and yield of the desired product, with fixed switching time and desorbent flow rate. The higher this feedstock flow rate, the better the performance of the SMB.

The flow rates in the unclosed bypass lines of the beds that are located in the other SMB zones are defined for each bed by the differential heads induced respectively in the bed and the bypass line.

The differential head in the adsorbent beds is essentially proportional to the flow rate while the differential head in the bypass lines is essentially proportional to the flow rate squared. The result is that any change in the flow rate will occur with a variation in synchronicity. Whereby zone 4 has the lowest flow rate, the bypass lines of the other zones will have a synchronicity that is necessarily higher than the synchronicity of the bypass lines of the zone 4. The synchronicity variations lead to being generally synchronous or under-synchronous (less than 100% synchronicity) in the zones with low flow rate, in particular in zone 4, and over-synchronous in zones with a higher flow rate, generally in zone 3.

Several reasons can lead to the closing of a bypass line in a given zone. In particular, when a fluid (feedstock or desorbent) is injected into a plate $P_i$, an injection line is used. This line is connected to a bypass line that is connected to said plate, i.e., either the bypass line $L_{i+1/i}$ or the bypass line $L_{i/i+1}$. Regardless of the bypass line that is used, it is then necessary to close said line using an all-or-nothing valve, a valve for adjusting flow rate, or a non-return valve or any other technical means that makes it possible to cancel the flow rate to ensure that only the injected fluid flows toward the plate $P_i$.

In the same way, when an effluent (extract or raffinate) is drawn off in a plate $P_i$, a draw-off line is used. This draw-off line is connected to a bypass line that is connected to said plate, i.e., either the bypass line $L_{i-1/i}$, or the bypass line $L_{i/i+1}$. Regardless of the bypass line used, it is then necessary to close said line using an all-or-nothing valve or a non-return valve or any other technical means that makes it possible to cancel the flow rate to ensure that the fluid is drawn off well from the plate $P_i$.

The bypass line to be closed for the injection or the draw-off depends in particular on the position of the injection and draw-off lines relative to the closing device of the bypass line. The position of an element (plate, bed, check mechanism, valve, . . . ) downstream from another element is defined relative to the direction of advance of the draw-off and introduction points during switching sequences.

For example, in the case where the effluent draw-off lines (raffinate or extract) are located upstream from the device for closing the bypass line (more simply: "upstream from the bypass line valve") and where the supply lines (of feedstock or desorbent) are located downstream from the isolating valve, When a fluid (feedstock or desorbent) is injected into the plate $P_i$, an injection line that is connected to the bypass line $L_{i-1/i}$ is used. It is then necessary to close the isolating valve of the bypass line $L_{i-1/i}$ to ensure that the injected fluid flows toward the plate $P_i$, When an effluent (extract or raffinate) is drawn off in the plate $P_i$, a draw-off line that is connected to the bypass line $L_{i/i+1}$ is used. It is then necessary to close the isolating valve of the bypass line $L_{i/i+1}$.

The closing of a bypass line for each injection and each draw-off induces the closing of a minimum of four bypass lines permanently. Other bypass lines can also be closed for other reasons.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

According to the Invention

An SMB unit that consists of 24 beds with a length of 1.1 m and with an inside radius of 3.5 m, with a feedstock injection, an injection of desorbent (can also be standardized eluant or solvent), a draw-off of extract and a draw-off of raffinate, is considered. The plates have two mixing chambers, whereby one is an injection box (feedstock and desorbent) and the other is a draw-off box (extract and raffinate).

The total volume $(V_i+V_{i+1}+VL_{i/i+1})$, where $VL_{i/i+1}$ is the volume of the bypass line of the plate $P_i$ in plate $P_{i+1}$, and where $V_i$ is the volume of the distribution/extraction system of the plate $P_i$, represents 3% of the volume of the bed between the plate $P_i$ and the plate $P_{i+1}$.

Figure 1:
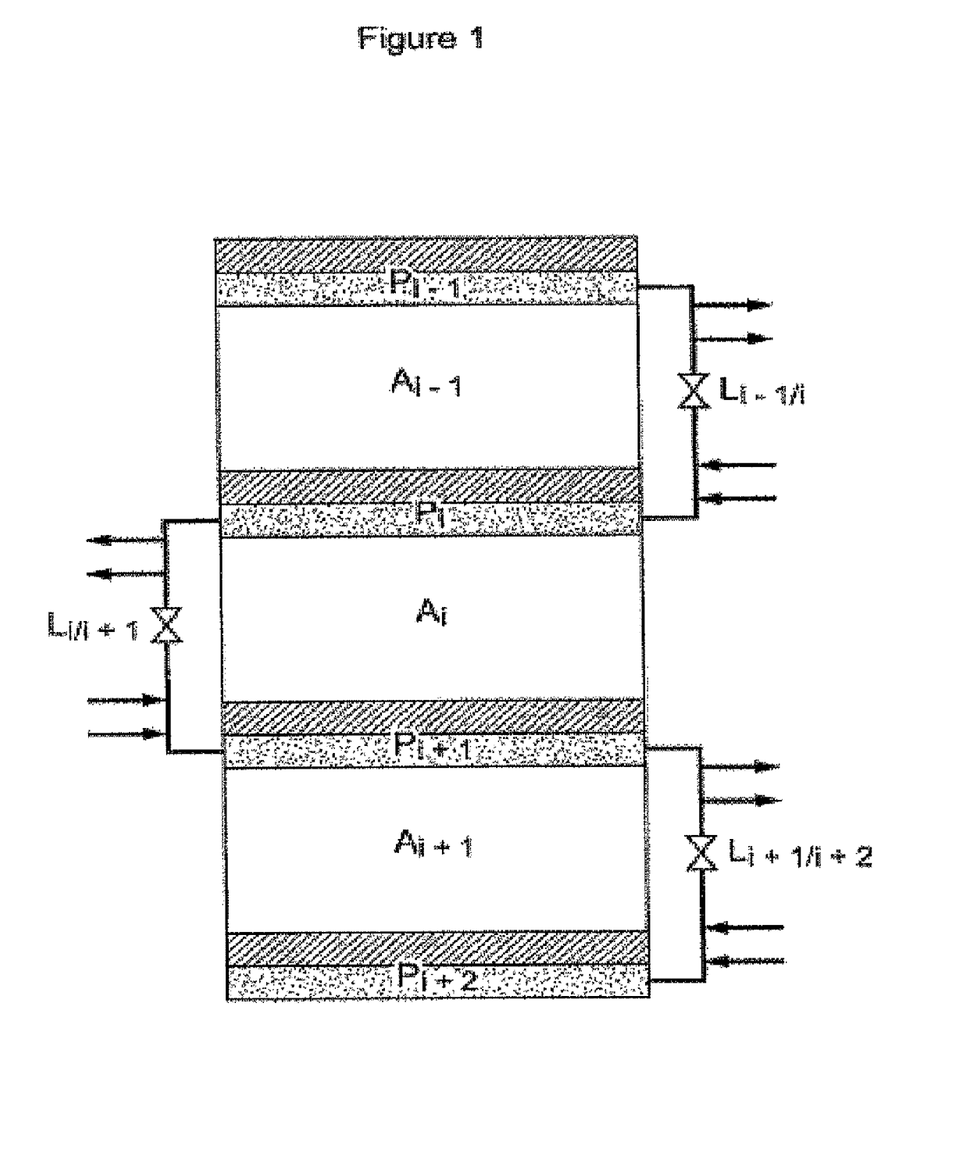
FIG. 1 shows a succession of 3 beds $P_{i-1}$, $P_i$, and $P_{i+1}$ that are part of a column in a simulated moving bed (SMB). The lines for drawing-off effluents (raffinate or extract) are located upstream from the isolating valve of the bypass line. The supply lines (of feedstock or desorbent) are located downstream from the isolating valve.

The lines for drawing-off effluents (raffinate or extract) are located upstream from the isolating valve of the bypass line (more simply: "upstream from the bypass line valve") and where the supply lines (of feedstock or desorbent) are located downstream from the isolating valve (FIG. 1).

When a fluid (feedstock or desorbent) is injected into the plate $P_i$, an injection line that is connected to the bypass line $L_{i-1/i}$ is used. It is then necessary to close the isolating valve of the bypass line $L_{i-1/i}$ to ensure that the injected fluid flows toward the plate $P_i$.

Figure 2A:
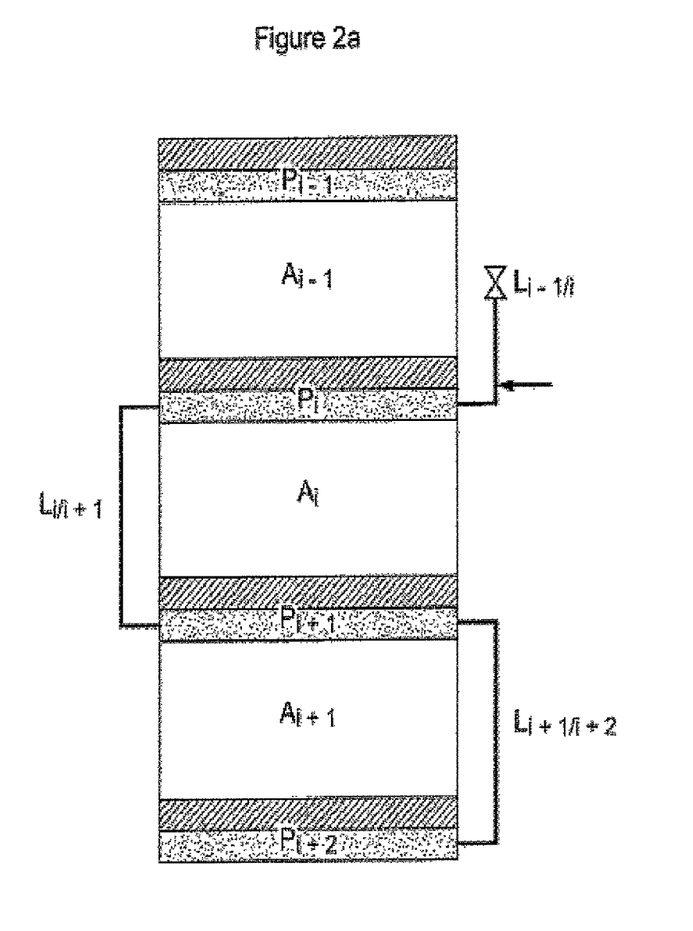
FIG. 2a shows an injection situation.
Figure 2B:
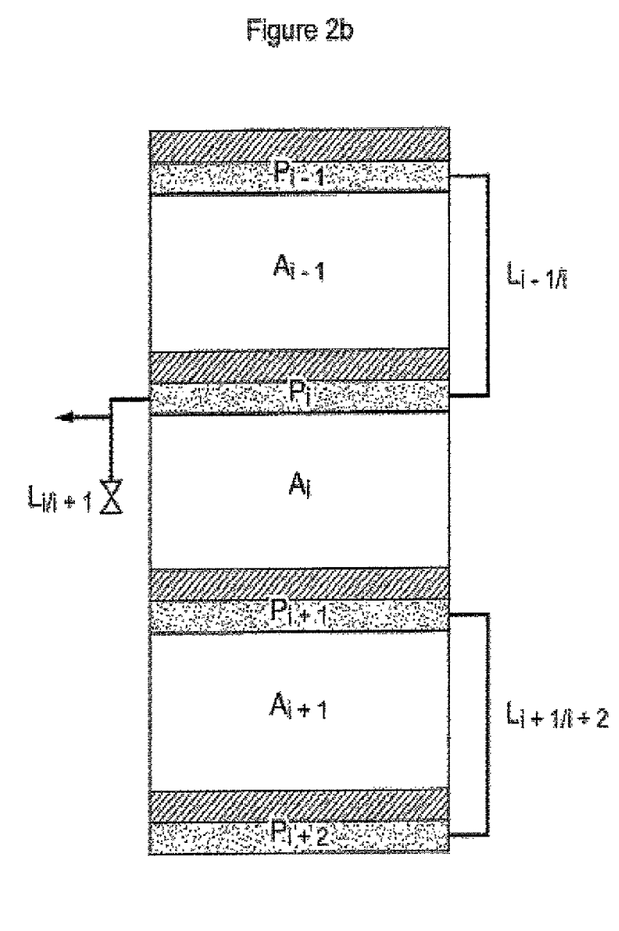
FIG. 2b shows a draw-off situation in a configuration of the column according to FIG. 1.

When an effluent (extract or raffinate) is drawn off into the plate $P_i$, a draw-off line that is connected to the bypass line $L_{i/i+1}$ is used. It is then necessary to close the isolating valve of the bypass line $L_{i/i+1}$ (FIG. 2).

The result is that the use of this type of bypass line leads to:

Closing two bypass lines in zone 2 (draw-off of the extract via a line that is connected to the bypass line of the first bed of the zone and injection of the feedstock via a line that is connected to the bypass line of the last bed of the zone), Closing two bypass lines in zone 4 (draw-off of the raffinate via a line that is connected to the bypass line of the first bed of the zone and injection of desorbent via a line that is connected to the bypass line of the last bed of the zone).

The beds are distributed according to the configuration 5/9/7/3, i.e., the distribution of the beds is as follows:

5 beds in zone 1;
9 beds in zone 2;
7 beds in zone 3;
3 beds in zone 4.

The adsorbent that is used is a BaX-type zeolite, and the eluant is para-diethylbenzene. The temperature is 175° C., and the pressure is 15 bar.

The feedstock consists of 20% paraxylene, 24% orthoxylene, 51% metaxylene, and 5% ethylbenzene. The switching period that is used is 70.8 seconds.

The injection flow rates of feedstock and desorbent are as follows:
6.80 m³/minute for the feedstock;
7.48 m³/minute for the desorbent;
or a solvent ratio of S/F=1.1. The purity is adjusted to 99.76%.

The bypass lines $L_{i/i+1}$ are equipped with valves with a variable degree of opening.

In the absence of automated means of regulating flow rates in the external bypass lines, the same degree of opening is set for all of the bypass lines of the system. Three different opening degree levels, denoted A, B and C in the table below, are used, inducing flow rates in the bypass lines and therefore different synchronicities as posted in the table below. We recall that the yield of PX is the ratio between the quantity of PX that is drawn off in the extract and the quantity of injected PX.

| Degree of Opening of the Valve | Zone 1 | Zone 2 | Zone 3 | Zone 4 | Yield of PX |
|---|---|---|---|---|---|
| A | 118% | 109% | 125% | 100% | 95.74% |
| B | 125% | 116% | 133% | 110% | 95.79% |
| C | 132% | 122% | 140% | 120% | 95.76% |

The table above shows that the degree of opening B is optimal. The yield is then 95.79%.

When the synchronicity according to the prior art is adjusted to 100% for all of the bypass lines by using automated means for regulating the flow rate in the bypass lines, a paraxylene purity of 99.76% and a yield of paraxylene of 95.80% are obtained by simulation.

The performances that are obtained without an automated means of adjusting the flow rate in the bypass lines are only very slightly set back relative to the prior art. In addition, this very slight loss in performance (−0.015% of yield) can easily be compensated by a very slight rise of the solvent ratio. The process according to the invention is therefore clearly attractive, in particular due to the very clear reduction of the investment relative to the prior art because of the absence of automated means of regulation on all of the bypass lines (24 in all).

EXAMPLE 2

According to the Invention

An SMB unit that consists of 24 beds with a length of 1.1 m and an internal radius of 3.5 m, with an injection of feedstock, an injection of eluant, a draw-off of extract and a draw-off of raffinate, is now considered.

The plates have two mixing chambers, whereby one is an injection box (feedstock and desorbent), and the other is a draw-off box (extract and raffinate). The total volume ($V_i + V_{i+1} + VL_{i/i+1}$), where $VL_{i/i+1}$ is the volume of the bypass line of the plate $P_i$ to the plate $P_{i+1}$ and where $V_i$ is the volume of the distribution/extraction system of the plate $P_i$, represents 3% of the volume of the bed that is between the plate $P_i$ and the plate $P_{i+1}$.

Figure 3:
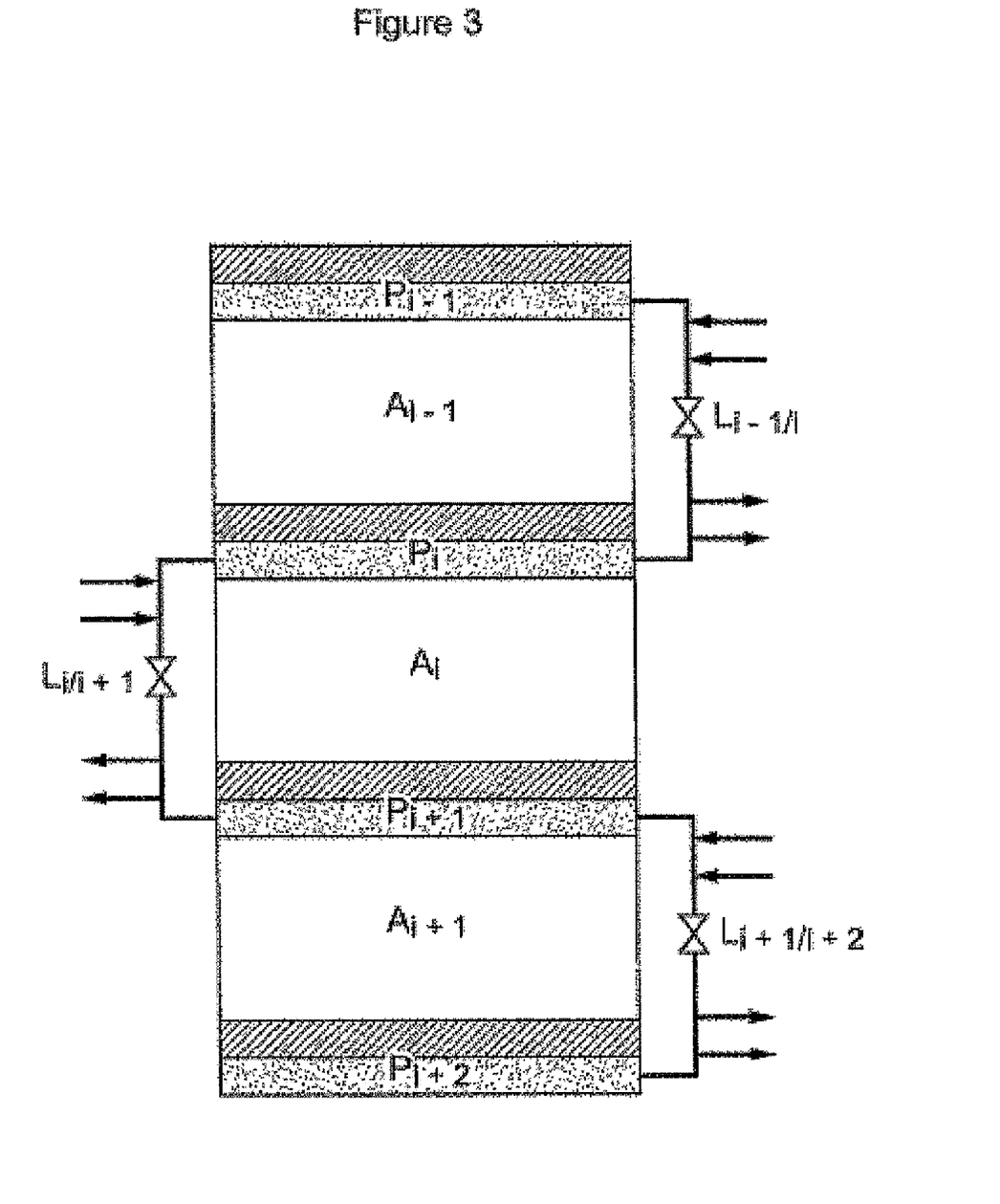
FIG. 3 shows a succession of 3 beds $P_{i-1}$, $P_i$, and $P_{i+1}$ that are part of a column in a simulated moving bed (SMB). The lines for drawing-off effluents (raffinate or extract) are located downstream from the isolating valve of the bypass line. The supply lines (of feedstock or desorbent) are located upstream from the isolating valve.

The points for drawing-off effluents (extract and raffinate) are now located downstream from the isolating valve of the bypass line, and the injection points (of feedstock or desorbent) are located upstream from the isolating valve (FIG. 3).

When a fluid (feedstock or desorbent) is injected into the plate $P_i$, an injection line that is connected to the bypass line $L_{i/i+1}$ is used. It is then necessary to close the isolating valve of the bypass line $L_{i/i+1}$ to ensure that the injected fluid flows toward the plate $P_i$.

Figure 4A:
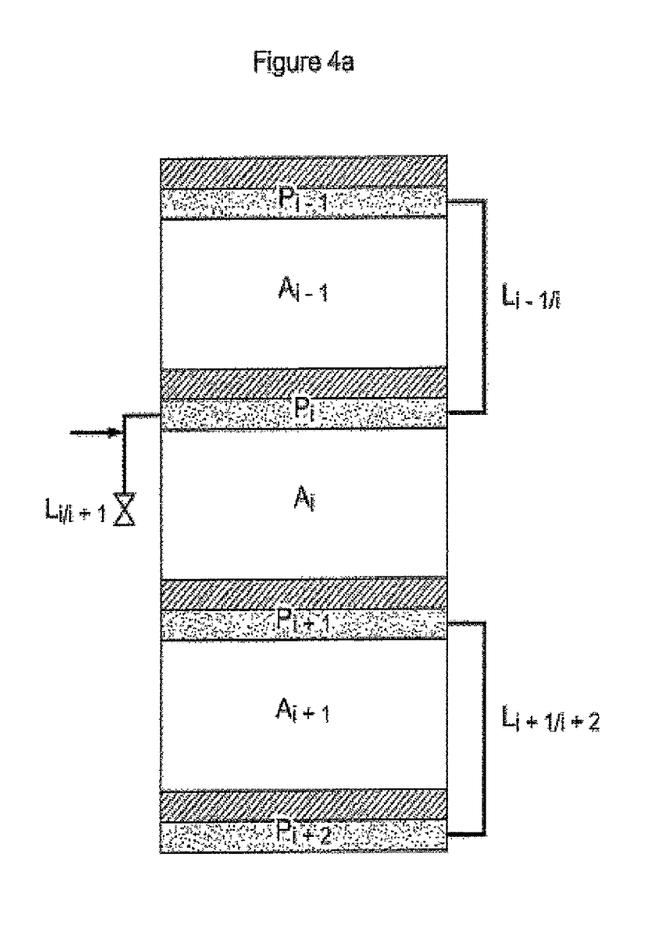
FIG. 4a shows an injection situation.
Figure 4B:
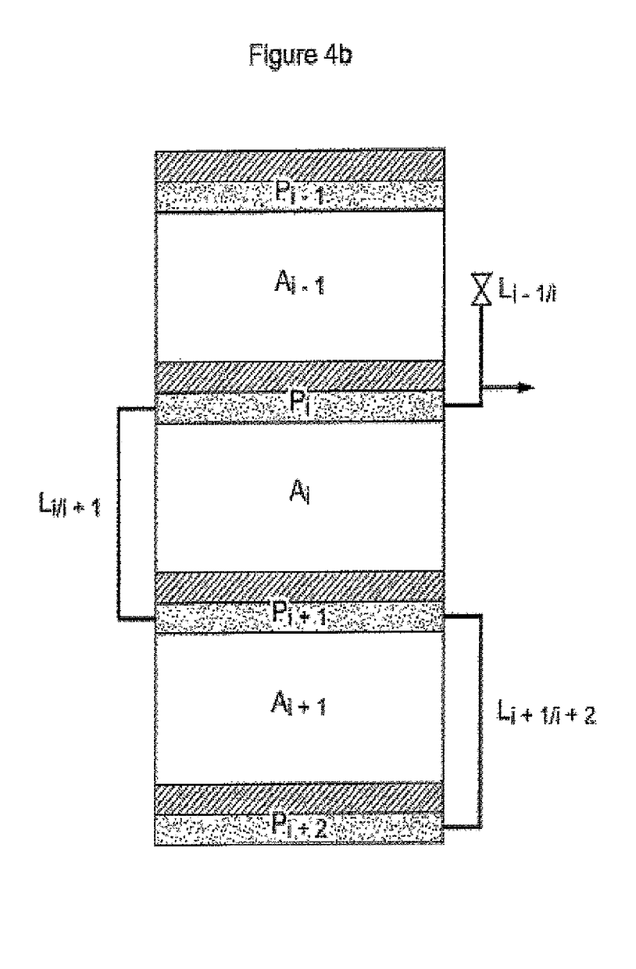
FIG. 4b shows a draw-off situation in a configuration of the column according to FIG. 3.

When an effluent (extract or raffinate) is drawn off in the plate $P_i$, a draw-off line that is connected to the bypass line $L_{i-1/i}$ is used. It is then necessary to close the isolating valve of the bypass line $L_{i-1/i}$ (FIG. 4).

The result is that the use of this type of bypass line leads to:
Closing two bypass lines in zone 1 (injection of desorbent via a line that is connected to the bypass line of the first bed of the zone and draw-off of the extract via a line that is connected to the bypass line of the last bed of the zone),
Closing two bypass lines of zone 3 (injection of the feedstock via a line that is connected to the bypass line of the first bed of the zone and draw-off of the raffinate via a line that is connected to the bypass line of the last bed of the zone).

The beds are distributed according to the configuration 5/9/7/3, i.e., the distribution of the beds is as follows:
5 beds in zone 1;
9 beds in zone 2;
7 beds in zone 3;
3 beds in zone 4.

The adsorbent that is used is a BaX-type zeolite, and the eluant is para-diethylbenzene. The temperature is 175° C., and the pressure is 15 bar.

The feedstock consists of 20% paraxylene, 24% orthoxylene, 51% metaxylene and 5% ethylbenzene. The switching period that is used is 70.8 seconds.

The injection flow rates of the feedstock and desorbent are as follows:
6.804 m³/minute for the feedstock;
7.484 m³/minute for the desorbent;
or a solvent ratio of S/F=1.1. The purity is adjusted to 99.76%.

The bypass lines $L_{i/i+1}$ are equipped with valves with a variable degree of opening.

In the absence of automated means for adjusting flow rates in the external bypass lines, the same degree of opening is set for all of the bypass lines of the system. Three different opening degree levels, denoted A, B and C in the table below, are used, inducing flows in the bypass lines and therefore different synchronicities as posted in the table below.

| Degree of Opening of the Valve | Zone 1 | Zone 2 | Zone 3 | Zone 4 | Yield of PX |
|---|---|---|---|---|---|
| A | 111% | 102% | 117% | 90% | 96.64% |
| B | 118% | 108% | 124% | 100% | 96.67% |
| C | 125% | 115% | 132% | 110% | 96.57% |

The table above shows that the degree of opening B is optimal. The yield is then 95.79%.

When the synchronicity according to the prior art is adjusted to 100% for all of the bypass lines by using automated means for regulating the flow rate in the bypass lines, a paraxylene purity of 99.76% and a yield of paraxylene of 96.63% are obtained by simulation.

Very surprisingly, it clearly appears that the use of a manual valve that is adjusted to the degree of opening B leads to an improved yield relative to the prior art. The process according to the invention therefore offers the double advantage of having a better performance than the processes according to the prior art and a clear reduction of the investment because of the absence of automated means of regulation on all of the bypass lines (24 in all).

The entire disclosures of all applications, patents and publications, cited herein and of corresponding French application Ser. No. 08/04638, filed Aug. 19, 2008 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for separation of a feedstock in a simulated moving bed (SMB) of a feedstock F in an SMB device having at least one column, wherein said column comprises a number of adsorbent beds separated by plates $P_i$, each comprising a distribution/extraction system, a process in which the feedstock F and a desorbent D are supplied, and at least one extract E and at least one raffinate R are drawn off, whereby the supply and draw-off points are offset over time by a value that corresponds to an adsorbent bed with a switching period ST, and that determines a number of operating zones of the SMB, including the four following primary zones:

A zone 1 for desorption of the compounds that are produced by extraction, between the supply of the desorbent D and the draw-off of the extract E, A zone 2 for desorption of the compounds that are produced with raffinate, between the draw-off of the extract E and the supply of the feedstock F, A zone 3 for the adsorption of the compounds that are produced by extraction, between the supply of the feedstock and the draw-off of the raffinate R, A zone 4, located between the draw-off of the raffinate R and the supply of the desorbent D, wherein the SMB device also comprises external bypass lines $L_{i/i+1}$ directly joining two successive plates $P_i$, $P_{i+1}$ that allow flushing of said plates, in which each of the bypass lines $L_{i/i+1}$ comprises non-automated means for adjusting the flushing flow rate, whereby flow rates on the different bypass lines have an over-synchronicity or an under-synchronicity based on the zone under consideration, and adjusting the flushing flow rate of the bypass lines so as to obtain the highest yield of desired product with fixed desorbent flow rate, feedstock flow rate, purity of the desired product and switching period, or the highest purity of the desired product, with fixed desorbent flow rate, feedstock flow rate, yield of desired product and switching period.

2. A process for separation according to claim 1 of paraxylene from a mixture of C8 aromatic hydrocarbons.

3. A process for separation according to claim 1 of metaxylene from a mixture of C8 aromatic hydrocarbons.

* * * * *